United States Patent [19]

Sanderson et al.

[11] Patent Number: 4,978,800

[45] Date of Patent: Dec. 18, 1990

[54] PRODUCTION OF DETERGENT RANGE ALCOHOLS AND KETONES USING ACETYLACETONATE CATALYSTS

[75] Inventors: John R. Sanderson, Leander; Edward T. Marquis; John F. Knifton, both of Austin, all of Tex.

[73] Assignee: Texaco Chemical Company, White Plains, N.Y.

[21] Appl. No.: 428,703

[22] Filed: Oct. 30, 1989

[51] Int. Cl.$^5$ .............................................. C07C 45/28
[52] U.S. Cl. ................................ 568/385; 568/398.8; 568/909.8; 568/910
[58] Field of Search ..................... 568/385, 909.8, 910, 568/910.5

[56] References Cited

U.S. PATENT DOCUMENTS

| | | | |
|---|---|---|---|
| 3,243,449 | 3/1966 | Winnick | 260/462 |
| 3,859,346 | 1/1975 | Camm et al. | 260/533 R |
| 3,879,467 | 4/1975 | Zajacek et al. | 568/385 |
| 4,459,427 | 7/1984 | Middleton et al. | 568/342 |

FOREIGN PATENT DOCUMENTS 0274909  7/1988  European Pat. Off. .

OTHER PUBLICATIONS

A. N. Bashkirov, et al., "Synthesis of Higher Aliphatic Alcohols by Direct Oxidation of Paraffinic Hydrocarbons", *Proc. World Pet. Cong.*, vol. 4, (1959), pp. 175-183.
N. J. Stevens, et al., "A New Route for Alcohols," *Chemical Engineering Progress*, vol. 64, No. 7, Jul. 1968, pp. 61-66.
D. Mansuy et al., "Metalloporphyrin–Catalyzed Hydroxylation of Cyclohexane by Alkyl Hydroperoxides: Pronounced Efficiency of Iron Porphyrins," *Angew. Chem. Int. Ed. Engl.*, vol. 19, No. 11, 1980, pp. 90-910.
M. J. Ijam, et al., "Liquid–Phase Oxidation of n-Dodecane in the Presence of Boron Compounds," *Ind. Eng. Chem. Prod. Res. Dev.*, vol. 20, 1981, pp. 315-319.
D. Mansuy, et al., "Alkane Hydroxylation Catalyxed by Metalloporphyrins: Evidence for Different Active Oxygen Species with Alkylhydroperoxides and Iodosobenzene as Oxidants," *Tetrahedron Letters*, vol. 23, No. 27, 1982, pp. 2781-2784.
H. J. Carlsen, "Ruthenium Catalyzed Oxidation of Alkanes," *Synthetic Communications*, vol. 17, No. 1, 1987, pp. 19-23.
"Porphyrin Catalysts for Olefin Epoxidation: A Literature Review 1985-86," *Catalysts in Chemistry*, vol. 21, No. 3, Mar. 1987, pp. 107-112.
M. M. Taqui-Khan, et al., "Ru(III)–EDTA Catalyzed Oxidation of Cyclohexane by Molecular Oxygen," *Journal of Molecular Catalysis*, vol. 45, 1988, pp. 51-56.
Y. V. Geletii, et al., "Oxidation of Saturated Hydrocarbons by Hydrogen Peroxide in Pyridine Solution Catalyzed by Copper and Iron Perchlorates," *J. Chem. Soc. Commun.*, 1988, pp. 936-937.
T. C. Lau, et al., "Ruthenium Catalyzed Oxidation of Alkanes with Alkylhydroperoxides," *J. Chem. Soc., Chem. Commun.*, 1988, pp. 1406-1407.
P. E. Ellis, et al., "Effect of Axial Azide on the Selective, Low Temperature Metalloporphyrin–Catalyzed Reactions of Isobutane with Molecular Oxygen," *J. Chem. Soc., Chem. Commun.*, 1989, pp. 1187-1188.

*Primary Examiner*—James H. Reamer
*Attorney, Agent, or Firm*—Jack H. Park; Kenneth R. Priem; David L. Mossman

[57] ABSTRACT

A process for the production of detergent range alcohols and ketones by reacting an alkane with a hydroperoxide in the presence of a transition metal acetylacetonate catalyst is described. Preferred hydroperoxides include cumene hydroperoxide and tertiary butyl hydroperoxide. The transition metal itself may be iron, ruthenium, chromium and mixtures thereof. If iron acetylacetonate is used as a catalyst, copper (II) acetate may be usefully employed as a co-catalyst.

4 Claims, No Drawings

PRODUCTION OF DETERGENT RANGE ALCOHOLS AND KETONES USING ACETYLACETONATE CATALYSTS

CROSS-REFERENCES TO RELATED APPLICATIONS

This application is related to U.S. Pat. application Ser. No. 07/428,812, filed Oct. 30, 1989, relating to the production of detergent range alcohols and ketones from alkanes and hydroperoxides in the presence of transition metal porphyrin catalysts, and to U.S. Pat. application Ser. No. 07/428,701, filed , Oct. 30, 1989, relating to the production of detergent range alcohols and ketones from alkanes and hydroperoxides in the presence of a dicyano bis-(1,10-phenanthrolene) iron (II) catalyst.

FIELD OF THE INVENTION

The invention relates to the catalytic production of detergent range alcohols and ketones and, in one aspect, more particularly relates to the production of detergent range alcohols and ketones from alkanes and hydroperoxides over a transition metal acetylacetonate catalyst.

BACKGROUND OF THE INVENTION

Producing alcohols and/or ketones from alkanes and other co-reactants is known. Often, such technology is pursued in attempts to discover viable processes for making useful chemicals directly from hydrocarbons, anticipating dwindling petrochemical feedstocks. In other instances, the co-reactant may be a by-product from another process, and an economical way of converting the by-product to a useful material may be needed. Sometimes a particular kind of alcohol or ketone, or mixture of alcohols and/or ketones is desired.

A number of publications provide a useful background in this technology. For example, A. N. Bashikirov, et al., in "Synthesis of Higher Aliphatic Alcohols by Direct Oxidation of Paraffinic Hydrocarbons," *Proc. World Pet. Cong.*, Vol. 4, (1959) pp. 175-183, report the "directed" synthesis of higher aliphatic alcohols via the liquid-phase oxidation of paraffinic hydrocarbons in the presence of boric acid, and by the selection of proper operating conditions which include a low oxygen concentration. Apparently, the boric acid serves as an esterification agent in the oxidation, and the conversion of alcohols into boric acid esters prevents them from further oxidation by interrupting the oxidative conversion chain at the alcohol stage. See also N. J. Stevens, et al., "A New Route for Alcohols," *Chemical Engineering Progress*, Vol. 64, No. 7, (1968) p. 61-66. Similarly, U.S. Pat. No. 3,243,449 teaches the oxidation of saturated hydrocarbons having 4 to 8 carbon atoms with molecular oxygen in the presence of metaboric acid or a less hydrated form of orthoboric acid, including boric anhydride, to produce borate esters. In this process, the contact temperature for the reactants is in the range of about 140° to 180° C., and the reaction is maintained so that the partial pressure of water in the exit gases, i.e., the vapor above the liquid reaction mixture, in psia is not greater than P, where P is given by the expression $\log_{10} P = 0.01112T - 0.259$.

In this same area is wOrk reported by M. J. Iljam, et al., in "Liquid-Phase Oxidation of n-Dodecane in the Presence of Boron Compounds," *Ind. Eng. Chem. Prod. Res. Dev.*, Vol. 20, (1981) pp. 315-319. The paper describes experiments on the production of neutral oxidation products rich in alcohols by the direct air oxidation of n-dodecane in the presence of boron compounds, such as tributoxyboroxine, boron trioxide, dibutoxyborane, etc. As with some of the previously discussed publications, lean oxygen-nitrogen mixtures (4% oxygen) are also used, here giving a mixture of six possible straight-chain $C_{12}$ alcohols.

In the absence of boric or other like catalysts, the direct oxidation of hydrocarbons produces alcohols and ketones in usually less than 60% selectivity, even at conversions of 20-30%. In the presence of boric acid, the selectivity to alcohols is increased to about 75-80% at 20-30% conversion, but even here, there are carboxylic acids and other by-products produced. In addition, the hydrolysis of the borate esters and isolation of the products is not a simple operation.

Paraffins having four to eight carbon atoms may be oxidized in the liquid phase with molecular oxygen in a reactor in which the manganese content is maintained in the range of 2 to 50 ppm to produce carboxylic acids, according to U.S. Pat. No. 3,859,346. The manganese may be in the form of manganese salts of carboxylic acids, e.g. manganese naphthenate, or in an aqueous solution, e.g. manganese acetate.

Also of general interest is Porphyrin Catalysts for Olefin Epoxidation: A literature review 1985-86," *Catalysts in Chemistry*, Vol. 21, No. 3, (1987) pp. 106-112. A number of oxidation processes are briefly mentioned, including ones involving iron and manganese porphyrin catalysts, primarily with a concentration on processes producing epoxides. The oxidation of cyclohexane to cyclohexanol and cyclohexanone by molecular oxygen catalyzed by ruthenium (III)-ethylenediaminetetraacetic acid in the presence and absence of the micelle cetyltrimethylammonium bromide (CTAB) is reported by M. M. Taqui Kahn, et al. in "Ru(III)-EDTA Catalyzed Oxidation of Cyclohexane by Molecular Oxygen," *Journal of Molecular Catalysis*, Vol. 45, (1988) pp. 51-56. The rate of oxidation was found to increase in the presence of CTAB. Similarly of interest is T. Lau, et al., "Ruthenium Catalysed Oxidation of Alkanes with Alkylhydroperoxides," *J. Chem. Soc., Chem. Commun.*, (1988) pp. 1406-1407, which reports that cis-[Ru(II)(L)-2(OH$_2$)$_2$]$^{2+}$ complexes may catalyze the oxidation of saturated hydrocarbons, such as cyclohexane, hexane and heptane, to alcohols and ketones by t-butylhydroperoxide. The L in the ruthenium catalyst formula may be substituted 2,2'-bipyridines of 1,10-phenanthrolines.

Of somewhat more pertinent interest are a number of publications describing research focussing on metalloporphyrin catalysts to make alcohols and ketones. For example, D. Mansuy, et al. in Metalloporphyrin-Catalyzed Hydroxylation of Cyclohexane by Alkyl Hydroperoxides: Pronounced Efficiency of Iron-Porphyrins," *Angew. Chem. Int. Ed. Engl.*, Vol 19, No. 11, (1980) pp. 909-910, describe the catalyzed hydroxylation of nonactivated alkanes, either by molecular oxygen in the presence of a reducing agent, or by two-electron oxidants. The researchers noted that the metalloporphyrins studied fell into three classes. First, the Cu(II)-, Ni(II)-, Zn(II)-, Mg(II)-, V(IV)- and Ti(IV)-porphyrins were found to be completely inactive under the reaction conditions used. The Co(TPP) and Os(TPP)(CO)(PY) compounds were found to catalyze cyclohexane oxidation, the former giving even a slightly faster reaction and better yields than Fe(TPP)(Cl), but both showing decreasing activity over time. The third group of Fe- and Mn(TPP)Cl were found to be true catalysts. A related study is reported in D. Mansuy, et al., Alkane Hydroxylation Catalyzed by Metalloporphyrins: Evidence for Different Active Oxygen Species with Alkyl-hydroperoxides and Iodosobenzene as Oxidants," *Tetrahedron Letters*, Vol. 23, No. 27, (1982) pp. 2781-2784. The comparative examination of cyclohexane and n-heptane hydroxylations by cumylhydroperoxide and iodosobenzene, catalyzed by various metalloporphyrins, indicated that different active oxygen species, presumably the cumyloxy radical and a metal-oxo intermediate were involved in these reactions. The metals used in the catalysts included iron, manganese, cobalt, rhodium and chromium.

Azido(tetraphenylporphyrinato) complexes of $Cr^{III}$, $Mn^{III}$ and $Fe^{III}$ are found to catalyze the selective, low temperature hydroxylation of isobutane with molecular oxygen, according to P. E. Ellis, et al. in "Effect of Axial Azide on the Selective, Low Temperature Metalloporphyrin-catalysed Reactions of Isobutane with Molecular Oxygen," *J. Chem. Soc., Chem. Commun.*, 1989, pp. 1187-88.

P.H.J. Carlsen in "Ruthenium Catalyzed Oxidation of Alkanes," *Synthetic Communications*, Vol. 17, No. 1, (1987) pp. 19-23 reports the use of a $RuCl_3$ catalyst in a solvent system containing $CCl_4-CH_3CN-H_2O$ and using sodium metaperiodate as the stoichiometric oxidation agent to oxidize a series of alkyl substituted alkanes. Norbornane and bicyclo[2.2.2]octane are oxidized to the corresponding ketone and adamantane is transformed to 1-adamantol. Another article of interest is Y.V. Geletti, et al., "Oxidation of Saturated Hydrocarbons by Hydrogen Peroxide in Pyridine Solution Catalysed by Copper and Iron Perchlorates," *J. Chem. Soc., Chem. Comm.*, (1988) pp. 936-937. The hydrocarbons used are cyclohexane and 2-methylbutane, which yield the ketone and alcohol with alkyl radicals not being intermediates.

Additionally of note is U.S. Pat. No. 4,459,427 which teaches that a mixture of the alcohol and ketone derivatives of alkanes may be produced by reacting the alkane with a hydrocarbyl hydroperoxide, e.g. t-butyl hydroperoxide in the presence of a catalyst. The catalyst may be an iron or manganese square planar complex having heterocyclic nitrogen-donor ligands, e.g. a porphyrin or phthalocyanine complex, which complex has either no axial ligands, for example, the lower valency or cationic complex, or an axial ligand which is non-coordinating or weakly-coordinating. Weakly coordinating ligands are defined as ligands having a coordinating power less than that of the chloride anion. The alkane employed is preferably a linear or branched alkane having from about 2 to 20 carbon atoms. Suitable complexes having no axial ligands are either neutral iron (II) and manganese (II) complexes, e.g. Fe(II)(TPP) and Mh(II)(TPP) or iron (III) and manganese (III) cationic complexes, such as [Fe(III)(TPP)]+ and [Mn(III)(TPP)]+.

Finally, European Patent Application 0274909 A2 is of interest. It submits that hydrocarbons, particularly lower molecular weight alkanes and cycloalkanes, may be oxidized with air or oxygen to form products such as alcohols, ketones and the like selectively in high yields when there is employed as the catalyst a highly active azide- or nitride-activated metal coordination complex having the structure:

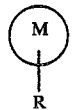

where M is a transition metal; the circle represents a ligand, and R is azide or nitride. Certain dimeric forms of these catalysts may also be employed. It is also discussed that Group IV through VIII transition metal nitrides are also effective oxidation catalysts for lower molecular weight hydrocarbons, such as alkanes. The discussion therein is also directed to certain novel azide-activated metal coordination complex catalysts, per se.

It will be appreciated that in the processes briefly described above, a wide variety of products is often achieved. In many of the reports on those processes, it was stated that a mixture of all possible products resulted. Thus, it would be advantageous if processes could be developed which would maximize the yield to a particularly useful product, in turn, by minimizing the yield to the other by-products. It would also be preferred that the reaction be able to be run at ambient temperature with catalysts that are readily obtainable so that the synthesis might be relatively simple and economical.

SUMMARY OF THE INVENTION

Accordingly, it is an object of the present invention to provide a process for the production of detergent range alcohols and ketones from hydrocarbons and peroxides using transition metal acetylacetonate catalysts.

It is another object of the present invention to provide a process for the production of detergent range alcohols and ketones that produces a minimum of by-products.

Another object of the invention to provide a method for making detergent range alcohols and ketones at ambient temperature and pressure conditions.

In carrying out these and other objects of the invention, there is provided, in one form, a process for the production of detergent range alcohols and ketones comprising reacting an alkane having from about 10 to 18 carbon atoms with a hydroperoxide selected from the group comprising cumene hydroperoxide, tertiary butyl hydroperoxide and mixtures thereof, in the presence of a transition metal acetylacetonate catalyst, where the transition metal is selected from the group consisting of iron, ruthenium, chromium and mixtures thereof.

DETAILED DESCRIPTION OF THE INVENTION

It has been discovered that detergent range alcohols and ketones may be produced from hydrocarbons and a hydroperoxide using metal acetylacetonate catalysts, particularly those where the transition metal is iron, ruthenium and/or chromium. In general, alkanes are difficult to react, hence, in many of the oxidation techniques discussed previously and those herein, a preparation step is required to provide an appropriate feedstock or co-reactant. In a preparation step, a second hydrocarbon containing a tertiary carbon, different from that used to make the alcohols and ketones, such as cumene or tertiary-butane, is oxidized to the corresponding hydroperoxide. Next, the hydroperoxide is reacted with the hydrocarbon in the presence of the catalyst, in accordance with the present invention. After isolation of the alcohols and ketones by distillation, the by-product carbinol derived from the hydroperoxide is reduced to the hydrocarbon and recycled to the hydroperoxide formation step. The overall result is the production of alcohols and ketones with a minimum of byproduct formation. For example, dodecanones and dodecanols are produced when n-dodecane is the starting, first hydrocarbon. The alcohols and ketones produced are useful intermediates for surfactants and detergents.

The second step, the reaction of interest, may be outlines as follows:

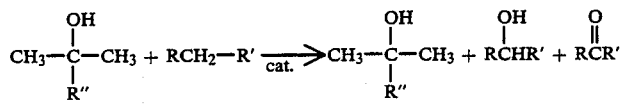

where R and R' are alkyl groups, taken together and with the central CH$_2$ group having 10 to 18 carbon atoms, and where R" is an alkyl or aryl group of one to ten carbon atoms. The RCH$_2$R' group may be a linear or branched hydrocarbon. In one aspect, these hydrocarbons have 11 to 16 carbon atoms.

Examples of suitable hydroperoxides are cumene hydroperoxide, t-butyl hydroperoxide and mixtures thereof; and examples of suitable alkanes are decane, undecane, n-dodecane, tridecane, tetradecane and the like, although it will be appreciated that the inventive process is not limited to these illustrative examples. As mentioned, the hydroperoxides may be prepared by the conventional air oxidation of the corresponding hydrocarbon. In one aspect, good results are obtained when the hydroperoxide is concentrated at least in the range of 60 to 90%. With respect to the hydrocarbons, pure hydrocarbons or mixtures may be employed.

A variety of transition metal acetylacetonate catalysts have been discovered as being suitable for the reaction. In one aspect, ruthenium acetylacetonate Ru(AcAc)$_3$, ferric or iron acetylacetonate Fe(AcAc)$_3$, chromium acetylacetonate Cr(AcAc)$_3$ are preferred. It is anticipated that certain ligands, co-catalysts and other additives, when used in conjunction with these catalyst systems, may provide beneficial results. Further, copper acetate Cu(OAc)$_2$ has been found to be a useful co-catalyst together with iron acetylacetonate.

The reaction conditions advantageous for this process are a temperature range from about 10° to 180° C., preferably from 20° to 100° C. or even 20° to 80° C. Atmospheric pressures are preferred for convenience, but elevated pressures may be suitable as well with certain modifications to the process.

As noted previously, an advantage of the process is that the carbinol may be converted back to the corresponding hydrocarbon and recycled to the oxidation step to produce more hydroperoxide. To take cumene hydroperoxide as a specific example, the by-product dimethyl phenyl carbinol may be reduced to cumene using known technology and recycled.

The invention is useful for the preparation of higher molecular weight alcohols and ketones, which are useful chemical intermediates for surfactants and detergents. Additionally, there is a minimum of by-product derived from the hydrocarbon. Various esters of the alcohols are useful lubricants, and some serve as plasticizers for plastics. As an added bonus, the reaction takes place at approximately ambient temperatures. The invention will be described further with reference to the following illustrative, detailed examples.

PROCEDURE 1A

This procedure will describe the preparation of the hydroperoxide, using cumene hydroperoxide (CHP) as an example. Cumene (190.0 g. 99% pure provided by Aldrich Chemical Co.) and cumene hydroperoxide (10.0 g., 85.7% pure provided by Aldrich Chemical Co.) were charged to a 250 ml resin flask equipped with stirrer, thermometer, heating mantle (Therm-O-Watch temperature regulator), water cooled condenser, and gas-sparging tube. The reaction mixture was purged with nitrogen and heated to the desired temperature ($\pm 2°$ C.). A zero-time sample was withdrawn for gas chromatography (GC) analysis and air (or pure oxygen) sparged through the reaction mixture at the required rate using a Gilmont flowmeter. The reaction mixture was heated at the desired temperature ($\pm 2°$ C.) and small samples (0.2–0.5 g.) withdrawn at various times. The samples were flushed with nitrogen and placed in small sealed vials until analysis by GC. At the end of the reaction, the reaction mixture was cooled to ambient temperature (while nitrogen was flushed through the solution) and then placed in a tared bottle. GC analysis was on a Hewlett-Packard 5890 gas chromatograph. The column was a 0.53 mm × 30 meter fused silica capillary column (DB-17, 50% phenyl methyl silicone). The conditions: 80°–275° C. after 4.0 min. 10#He 190 cc split, 0.5 $\mu$l injection, 80° C. injection temperature. Some typical results are shown in Table IA. The examples are numbered starting at Example 101 to easily distinguish them from the more important inventive examples, which begin at "Example 1". Cumene may be distilled off to produce CHP of the desired concentration for Procedure 2, also called the second step.

TABLE IA

| | | | | Peroxidation of Cumene | | | | | |
|---|---|---|---|---|---|---|---|---|---|
| Ex. No. | Time (hrs.) | Temp. °C. | Fl Rt.[1] (ml/m) | Oxygen form | Cumene Conv. % | Selectivity %[2] | | | |
| | | | | | | CHP | DMPC | ACETP | MeSTY | UNK. |
| 101 | 1.00 | 110.0 | 100.0 | A | 1.63 | 90.31 | 6.85 | 1.77 | 0.53 | 0.00 |
| 102 | 2.00 | 110.0 | 100.0 | A | 4.47 | 94.00 | 3.99 | 1.09 | 0.34 | 0.06 |
| 103 | 3.00 | 110.0 | 100.0 | A | 7.90 | 95.13 | 3.17 | 0.86 | 0.25 | 0.07 |
| 104 | 4.00 | 110.0 | 100.0 | A | 11.82 | 94.63 | 3.68 | 0.92 | 0.21 | 0.06 |
| 105 | 5.00 | 110.0 | 100.0 | A | 15.78 | 93.91 | 4.12 | 1.23 | 0.18 | 0.06 |
| 106 | 6.00 | 110.0 | 100.0 | A | 20.52 | 92.69 | 4.65 | 1.90 | 0.15 | 0.10 |
| 107 | 7.00 | 110.0 | 100.0 | A | 24.19 | 92.19 | 5.21 | 1.44 | 0.14 | 0.10 |
| 108 | 0.50 | 120.0 | 100.0 | A | 1.76 | 92.79 | 4.57 | 1.54 | 0.50 | 0.00 |
| 109 | 1.00 | 120.0 | 100.0 | A | 3.57 | 92.97 | 4.37 | 1.62 | 0.46 | 0.07 |

TABLE IA-continued

Peroxidation of Cumene

| Ex. No. | Time (hrs.) | Temp. °C. | Fl Rt.[1] (ml/m) | Oxygen form | Cumene Conv. % | Selectivity %[2] | | | | |
|---|---|---|---|---|---|---|---|---|---|---|
| | | | | | | CHP | DMPC | ACETP | MeSTY | UNK. |
| 110 | 2.00 | 120.0 | 100.0 | A | 7.63 | 92.78 | 4.56 | 1.64 | 0.41 | 0.09 |
| 111 | 3.00 | 120.0 | 100.0 | A | 12.54 | 92.73 | 4.77 | 1.54 | 0.35 | 0.11 |
| 112 | 4.00 | 120.0 | 100.0 | A | 16.57 | 91.66 | 5.55 | 1.77 | 0.33 | 0.17 |
| 113 | 5.00 | 120.0 | 100.0 | A | 20.67 | 90.55 | 6.45 | 2.03 | 0.29 | 0.17 |
| 114 | 6.00 | 120.0 | 100.0 | A | 24.98 | 88.78 | 7.21 | 2.35 | 0.26 | 0.32 |
| 115 | 7.00 | 120.0 | 100.0 | A | 28.88 | 85.07 | 6.38 | 6.80 | 0.24 | 0.35 |
| 116 | 0.50 | 130.0 | 100.0 | A | 1.32 | 90.70 | 5.30 | 2.09 | 1.22 | 0.00 |
| 117 | 1.00 | 130.0 | 100.0 | A | 3.18 | 91.44 | 4.82 | 1.98 | 1.02 | 0.16 |
| 118 | 1.50 | 130.0 | 100.0 | A | 5.33 | 90.69 | 5.44 | 2.28 | 0.90 | 0.17 |
| 119 | 2.00 | 130.0 | 100.0 | A | 7.89 | 90.16 | 5.90 | 2.47 | 0.79 | 0.18 |
| 120 | 3.00 | 130.0 | 100.0 | A | 12.43 | 86.91 | 7.48 | 3.47 | 0.70 | 0.22 |
| 121 | 4.00 | 130.0 | 100.0 | A | 17.53 | 85.07 | 9.63 | 3.91 | 0.59 | 0.29 |
| 122 | 5.00 | 130.0 | 100.0 | A | 23.14 | 81.44 | 11.53 | 4.61 | 0.47 | 0.50 |
| 123 | 6.00 | 130.0 | 100.0 | A | 28.31 | 78.99 | 13.97 | 5.21 | 0.38 | 0.64 |
| 124 | 1.00 | 140.0 | 100.0 | A | 4.56 | 87.48 | 7.28 | 3.34 | 1.38 | 0.00 |
| 125 | 2.00 | 140.0 | 100.0 | A | 9.48 | 80.96 | 12.15 | 5.10 | 1.26 | 0.00 |
| 126 | 1.00 | 110.0 | 200.0 | B | 1.41 | 96.65 | 2.24 | 0.56 | 0.00 | 0.00 |
| 127 | 2.00 | 110.0 | 200.0 | B | 4.71 | 95.12 | 3.21 | 0.86 | 0.21 | 0.05 |
| 128 | 3.00 | 110.0 | 200.0 | B | 9.16 | 94.47 | 3.88 | 0.94 | 0.16 | 0.04 |
| 129 | 4.00 | 110.0 | 200.0 | B | 13.62 | 93.82 | 4.45 | 1.04 | 0.14 | 0.05 |
| 130 | 5.00 | 110.0 | 200.0 | B | 18.74 | 93.17 | 5.08 | 1.09 | 0.12 | 0.04 |
| 131 | 6.00 | 110.0 | 200.0 | B | 23.19 | 92.44 | 5.42 | 1.48 | 0.11 | 0.05 |
| 132 | 1.00 | 120.0 | 200.0 | B | 6.22 | 93.72 | 4.05 | 1.35 | 0.28 | 0.06 |
| 133 | 2.00 | 120.0 | 200.0 | B | 15.67 | 91.15 | 5.47 | 1.74 | 0.18 | 0.07 |
| 134 | 3.00 | 120.0 | 200.0 | B | 26.74 | 89.99 | 7.19 | 2.13 | 0.13 | 0.07 |
| 135 | 4.00 | 120.0 | 200.0 | B | 37.51 | 87.09 | 8.84 | 2.46 | 0.10 | 0.09 |
| 136 | 5.00 | 120.0 | 200.0 | B | 46.41 | 85.83 | 13.19 | 0.00 | 0.12 | 0.16 |
| 137 | 6.00 | 120.0 | 200.0 | B | 53.16 | 82.16 | 15.76 | 0.00 | 0.20 | 0.40 |
| 138 | 1.00 | 130.0 | 200.0 | B | 14.51 | 90.57 | 6.12 | 2.46 | 0.24 | 0.08 |
| 139 | 2.00 | 130.0 | 200.0 | B | 36.36 | 85.27 | 9.06 | 4.90 | 0.12 | 0.14 |
| 140 | 3.00 | 130.0 | 200.0 | B | 55.21 | 79.77 | 14.61 | 4.38 | 0.12 | 0.26 |
| 141 | 4.00 | 130.0 | 200.0 | B | 64.87 | 67.65 | 12.48 | 15.21 | 0.49 | 2.21 |
| 142 | 5.00 | 130.0 | 200.0 | B | 65.57 | 50.07 | 22.72 | 9.94 | 1.40 | 10.86 |
| 143 | 1.00 | 140.0 | 200.0 | B | 25.92 | 86.01 | 8.99 | 4.03 | 0.26 | 0.21 |
| 144 | 2.00 | 140.0 | 200.0 | B | 53.19 | 75.31 | 11.98 | 11.41 | 0.16 | 0.54 |
| 145 | 3.00 | 140.0 | 200.0 | B | 64.33 | 59.88 | 27.95 | 7.67 | 0.55 | 1.93 |

[1]CHP = cumene hydroperoxide, DMPC = dimethylcarbinol, ACETP = acetophenone, MeSTY = α-methylstyrene, UNK. = sum of unknowns with retention higher than CHP.
[2]Flow rate for air (A) or pure oxygen (B)

PROCEDURE 1B

A mixture of tert-butyl hydroperoxide, tert-butyl alcohol and acetone in a ratio of 65:34:1, equivalent to 5–6% isobutane conversion, and finely divided sodium pyrophosphate (0.01 wt. % basis total) was charged to the autoclave through a small vent hole near the top of the reactor. The autoclave was then sealed and isobutane pressured in. The mixture was then heated to the desired temperature. The stirring rate was 300 rpm. Oxygen was added in ~1 g. increments until a pressure of 150–200 psi over autogeneous was reached. Oxygen was then added only after the pressure had dropped 50 psi. The reaction was continued for the desired time and near the end of the reaction, no more oxygen was added so that a large excess of oxygen would not be present to create an explosive mixture. The reaction was cooled as rapidly as possible to ambient temperature and the contents pressured out into a tared stainless steel bomb with 300 psi nitrogen. The weight % products were determined by GC analysis of bomb contents.

TABLE IB

Isobutane Oxidation at 145° C.

| Ex. | Time (Hr.) | IB (Wt. %) | THBP (Wt. %) | TBA (Wt. %) | Acetone[1] (Wt. %) |
|---|---|---|---|---|---|
| 146 | 2.0 | 73.915 | 18.114 | 7.678 | 0.155 |
| 147 | 2.5 | 69.745 | 20.847 | 9.021 | 0.197 |
| 148 | 3.5 | 59.101 | 26.964 | 13.188 | 0.406 |
| 149 | 4.0 | 55.917 | 28.347 | 14.972 | 0.460 |
| 150 | 2.0 | 74.712 | 17.751 | 7.188 | 0.135 |
| 151 | 2.5 | 70.923 | 19.815 | 8.833 | 0.285 |
| 152 | 3.0 | 65.161 | 23.277 | 10.858 | 0.271 |
| 153 | 4.0 | 55.307 | 28.742 | 15.247 | 0.427 |
| 154 | 4.0 | 55.207 | 28.494 | 15.526 | 0.448 |
| 155 | 2.0 | 75.814 | 17.130 | 6.850 | 0.122 |
| 156 | 3.0 | 66.495 | 22.604 | 10.453 | 0.251 |
| 157 | 4.0 | 55.593 | 28.188 | 13.720 | 0.422 |
| 158 | 4.0 | 53.980 | 28.728 | 15.613 | 0.499 |
| 159 | 1.0 | 83.183 | 12.252 | 4.468 | 0.037 |
| 160 | 3.0 | 63.706 | 23.693 | 11.716 | 0.309 |
| 161 | 3.16 | 62.065 | 24.478 | 12.352 | 0.332 |

PROCEDURE 2

This procedure will outline the inventive process for producing detergent range alcohols and ketones. n-Dodecane (50.0 g.) and the indicated catalyst(s) were charged to a ml flask equipped with stirrer, dropping funnel and 250 thermometer. Cumene hydroperoxide (80%) was added slowly to the stirred reaction mixture over several hours. The temperature was maintained by the use of a water bath or a heating mantle. At the end of the reaction, the mixture was filtered and analyzed by GC and/or GC/IR (infra-red spectroscopy). The results are shown in the following Table II. The alcohols and ketones may be isolated by distillation. The by-products dimethyl phenyl carbinol and α-methyl styrene may be reduced and recycled.

TABLE II

Detergent Range Ketones and Alcohols from Higher Molecular Weight Hydrocarbons and Cumene Hydroperoxide Using Ruthenium, Iron and Chromium Catalysts

| Ex. | Catalyst(s)[1] | Wt., grams | Time, hours | Temp. °C.[2] | Wt. % $C_{12}$ Products Ketone | Alcohol |
|---|---|---|---|---|---|---|
| 1 | Ru(AcAc)$_3$ | 0.05 | 20.0 | 30 | 2.68 | 0.79 |
| 2 | Ru(AcAc)$_3$ IM | 0.05 0.025 | 23.0 | 30 | 1.19 | 0.45 |
| 3 | Ru(AcAc)$_3$ IM | 0.05 0.05 | 23.0 | 30 | 0.41 | 0.12 |
| 4 | Ru(AcAc)$_3$ Fe(AcAc)$_3$ | 0.05 0.02 | 23.0 | 30 | 2.45 | 0.48 |
| 5 | Ru(AcAc)$_3$ Cr(AcAc)$_3$ | 0.05 0.02 | 23.0 | 30 | 2.43 | 0.40 |

Interestingly, the yields using imidazole as a ligand with ruthenium acetylacetonate, in Examples 2 and 3, were poorer than when ruthenium acetylacetonate was used alone (Example 1).

EXAMPLES 6-9

Use of Iron Acetylacetonate as Catalyst

These next Examples will illustrate the use of copper acetate and iron acetylacetonate each alone and together as co-catalysts.

Procedure: A 250 ml flask was charged with catalyst(s), n-dodecane (30.0 g.), tert-butyl alcohol (35.0 g.), and this mixture was vigorously stirred. Next, 55.0 g. of 54.6% tert-butyl hydroperoxide solution in tert-butyl alcohol was added over several hours The reactions at 25° C. were controlled by a water bath. The reactions at 80° C. were controlled by means of a Therm-O-Watch temperature regulator. The reactors were stirred for a total of 20 hours. At the end of the reaction, the reaction mixture was analyzed by GPC. The results are shown in Table III.

TABLE III

Use of Copper Acetate and Iron Acetylacetonate Catalysts

| Ex | Catalyst | (g) | Temp. C. | Wt. % TBHP | Wt. % Ketone | Wt. % Alcohol | Wt. % Total | Wt. % DTBP |
|---|---|---|---|---|---|---|---|---|
| 6 | Cu(OAc)$_2$ | 0.50 | 25 | 17.77 | 0.094 | ≈0 | 0.094 | 0.12 |
| 7 | Fe(AcAc)$_3$ | 0.50 | 80 | 14.74 | 0.50 | 0.036 | 0.86 | 0.11 |
| 8 | Fe(AcAc)$_3$ Cu(OAc)$_2$ | 0.50 0.10 | 80 | 11.51 | 1.44 | 0.98 | 2.42 | 0.26 |
| 9 | Fe(AcAc)$_3$ Cu(OAc)$_2$ | 0.50 0.05 | 80 | 7.16 | 2.75 | 1.45 | 4.20 | 0.40 |

It is of interest that a greater yield to ketone and alcohol products is achieved with a combination of the copper acetate and iron acetylacetonate catalysts than with either catalyst alone.

Many modifications may be made in the process of this invention without departing from the spirit and scope thereof which are defined only in the appended claims. For example, one skilled in the art may discover a new ligand or co-catalyst, or reaction condition which may not be explicitly recited herein, but which is nevertheless anticipated, and which would give desirable results.

| GLOSSARY | |
|---|---|
| CHP | Cumene hydroperoxide |
| Cr(AcAc)$_3$ | Chromium (III) acetylacetonate |
| Cu(OAc)$_2$ | Copper (II) acetate |
| DTBP | Di-tert-butyl peroxide |
| Fe(AcAc)$_3$ | Iron or ferric (III) acetylacetonate |
| IM | Imidazole |
| Ru(AcAc)$_3$ | Ruthenium (III) acetylacetonate |
| TBA | tert-Butyl alcohol |
| TBHP | tert-Butyl hydroperoxide |

We claim:

1. A process for the production of a mixture of detergent range alcohols and ketones having from about 10 to 18 carbon atoms comprising reacting an alkane having from about 10 to 18 carbon atoms with a hydroperoxide in the presence of a transition metal acetylacetonate catalyst where the catalyst is selected from the group consisting of (1) ruthenium acetylacetonate alone, (2) ruthenium acetylacetonate and iron acetylacetonate as a co-catalyst, (3) ruthenium acetylacetonate and chromium acetylacetonate as a co-catalyst, (4) iron acetylacetonate and copper acetate as a co-catalyst and mixtures thereof.

2. The process of claim 1 where the hydroperoxide is selected from the group consisting of cumene hydroperoxide, tertiary butyl hydroperoxide, and mixtures thereof.

3. The process of claim 1 where the reaction is conducted at a temperature between about ambient and 180° C., and at about a atmospheric pressure.

4. A process for the production of a mixture of detergent range alcohols and ketones having from about 10 to 18 carbon atoms comprising reacting an alkane having from about 10 to 18 carbon atoms with a hydroperoxide selected from the group consisting of cumene hydroperoxide, tertiary butyl hydroperoxide, and mixtures thereof at a temperature between about ambient and 180° C., and at about atmospheric pressure in the presence of an iron acetylacetonate catalyst and copper acetate as a co-catalyst.

* * * * *